United States Patent [19]

Schmitt et al.

[11] 4,389,497

[45] Jun. 21, 1983

[54] USE OF AGGLOMERATES OF SILICIC ACID AS FILLERS IN DENTAL MATERIALS

[75] Inventors: Werner Schmitt; Robert Purrmann, both of Starnberg; Peter Jochum, Hechendorf; Heinz-Joachim Hübner, Seefeld, all of Fed. Rep. of Germany

[73] Assignee: Espe Fabrik parmazeutischer Präparate GmbH, Fed. Rep. of Germany

[21] Appl. No.: 285,115

[22] PCT Filed: Nov. 21, 1980

[86] PCT No.: PCT/EP80/00135

§ 371 Date: Jul. 22, 1981

§ 102(e) Date: Jul. 22, 1981

[87] PCT Pub. No.: WO81/01366

PCT Pub. Date: May 28, 1981

[30] Foreign Application Priority Data

Nov. 22, 1979 [DE] Fed. Rep. of Germany ....... 2947129

[51] Int. Cl.³ .......................... A61K 5/06; C08K 3/36
[52] U.S. Cl. .................................... 523/116; 523/212;
523/216; 524/493; 524/560; 524/786; 524/789; 524/790; 524/847
[58] Field of Search .............. 523/115, 116, 212, 216;
524/493, 560, 789, 790, 847, 786

[56] References Cited

U.S. PATENT DOCUMENTS

| | | | |
|---|---|---|---|
| 3,066,112 | 11/1962 | Bowen | 523/116 |
| 3,472,459 | 10/1969 | Pfeifer et al. | 241/19 |
| 3,532,473 | 10/1970 | Biegler et al. | 264/117 |
| 3,597,389 | 8/1971 | Taylor | 523/116 |
| 3,825,518 | 7/1974 | Foster et al. | 523/116 |
| 3,914,341 | 10/1975 | Kliment et al. | 260/31.6 |
| 3,991,008 | 11/1976 | Temin et al. | 523/116 |
| 4,220,582 | 9/1980 | Orlowski et al. | 260/998.11 |
| 4,267,097 | 5/1981 | Michl et al. | 260/998.11 |
| 4,277,536 | 7/1981 | Podszun et al. | 428/402 |
| 4,281,991 | 8/1981 | Michl et al. | 260/998.11 |

FOREIGN PATENT DOCUMENTS

| | | |
|---|---|---|
| 11734 | 5/1980 | European Pat. Off. . |
| 26398 | 4/1981 | European Pat. Off. . |
| 1467437 | 12/1968 | Fed. Rep. of Germany . |
| 2403211 | 7/1975 | Fed. Rep. of Germany . |
| 1488403 | 10/1977 | United Kingdom . |

OTHER PUBLICATIONS

Chem. Abs. vol. 83, #16, Oct. 20, 1975, p. 355, col. 1, 136949n.
Research Disclosure #162, Oct. 1977, "New Dental Materials" p. 80, col. 1, 16269.
C.A. 83-136949 (16) Tanaka (showa Pharm), Japan 7548021, JP98112 (1973).
Derwent Abst. 728079, (1969), "Mineral Agglomerate" Belgium Patent Sanders.

Primary Examiner—John C. Bleutge
Assistant Examiner—Herbert J. Lilling
Attorney, Agent, or Firm—Burns, Doane, Swecker & Mathis

[57] ABSTRACT

The invention relates to the use of agglomerates of silicic acid having an average agglomerate size of 0.5 to 50 μm, containing primary particles of silicic acid having an average particle size of 1 to 100 nm and serving as filler in dental materials on the basis of ethylenically unsaturated polymerizable monomers. This reinforcing filler is practically colorless and can be blended in considerable quantity into the polymerizable monomer material especially mono-functional and di-functional as well as polyfunctional esters of the acrylic acid and the methacrylic acid and yields a satisfactorily processable plastically deformable paste. If necessary, the agglomerated silicic acid is used together with non-agglomerated micro-fine silicic acid of an average particle size of 1 to 100 nm. The shaped bodies obtained after the curing of the polymerizable material with the fillers show superior compressive strength, low thermal expansion, high colour stability and low water absorption, and moreover can be finished to high luster. The agglomerated fillers provided according to the invention are generally suitable for tooth filling preparations and tooth restoration materials as well as for the production of artificial teeth.

16 Claims, No Drawings

USE OF AGGLOMERATES OF SILICIC ACID AS FILLERS IN DENTAL MATERIALS

As it is known from the U.S. Pat. No. 3,066,112, to the hardenable dental materials on the basis of ethylenically unsaturated, polymerizable monomers of which especially the mono-functional and di-functional as well as poly-functional esters of the acrylic acid and methacrylic acid have achieved considerable practical use, higher amounts of inoganic fillers are added for the reduction of the shrinkage during polymerization, decrease of the thermal expansion coefficient and increase of hardness of the obtained polymerisates. The fraction of inert inorganic fillers can amount up to more than 80% of the total material in such dental permanent filling materials. As fillers e.g. quartz, quartz glass or silicate glasses like lithiumaluminium silicate or barium silicate glass are used as fine powder. The particle sizes of these fillers are within the range of 1 $\mu$m to approximately 100 $\mu$m, the average particle diameter being generally in the magnitude of approximately 10 $\mu$m.

Disadvantageous upon use of these fillers is the fact that the dental materials produced therefrom do not yet have a satisfying abrasion resistance and have surface roughness upon utilisation as tooth fillings. Due to the mediocre abrasion resistance, the tooth filling materials could not be used with the mentioned fillers in the molar field where the amalgam fillings are still predominant despite the toxicologically critical mercury.

The surface roughness of the mentioned materials leads additionally to problems upon use in the anterior tooth area since the depositing of dental plaque is promoted, thereby causing discolorations as well as marginal secondary caries.

From the DE-OS No. 24 03 211, there is known that very finely divided fillers, like micro-fine silicic acid (silicon dioxide gel) or aluminium oxide, having particle sizes within the range of 5–700 nm, yield well-polishable shaped bodies after curing of the dental material produced therewith. As can be seen from the articles of R. Schäfer in "Dental Echo", Vol. 49, 136 (1979) and A. Groß in "Chemie in unserer Zeit", 13th Annual Set, page 142 (1979), no workable pastes having high contents of fillers as required for the dental application in the dental practice can be obtained with these micro-fine fillers which have a very large specific surface. It has been shown that upon blending of the micro-fine silicic acid, e.g. of the pyrolitically produced silicon dioxide gel, into the liquid monomer, a thickening of this monomer to a honey-like, stringy and adhesive mass is firstly obtained and then is suddenly converted into a bittle mass upon continuous addition of silicic acid which mass finally dissolves in a freely flowing powder. Thus, only masses of salve-like or powdery consistency can be produced. In these references, it is now pointed out that the micro-fine filler shall be firstly premixed and prepolymerised with a polymerizable monomer. The solid product so obtained is crushed and finely ground. This pulverized splinter polymerisate is then used as actual filler in the hardenable dental material.

In this manner, however, very high fractions of inorganic fillers are not achievable in the dental materials since, according to this known method the splinter polymerisate to be incorporated in the monomer consists considerably of organic substance, already.

Therefore, upon utilisation of this filler, a higher thermal expansion coefficient must be accepted thereby partly compensating the aspired advantage of having a high filler fraction within the polymerizable dental material. In case the filling material and the tooth substance have a considerably different thermal expansion coefficient, the so-called "pump effect" is obtained caused by the change of temperature e.g. by ingestion. Through the formed marginal gap, bacteria can penetrate and lead to secondary caries or to damages of the pulp in deep cavities. In addition, the micro-fine silicic acid must be mixed very intensively with the monomer fluid during the production of the pre-polyfmerisate in order to achieve a uniform coating of the particles of the silicon dioxide powder with the hardenable monomer. The cold-hardening monomer preparations are hardly suitable due to the relatively rapid course of polymerization. Therefore, the method of the hot-polymerization must be used. The relatively high temperatures obtained therewith lead, however, to discolorations since the curing shall occur rather intensively in order to obtain a hard and brittle filling material which is easily pulverable. Due to this more or less considerably yellowish colored pre-polymerisate powder, it is difficult to obtain dental materials in light coloring and to secure a uniform colour adjustment during the technical production. Although the micro-fine, pyrogenic silicic acid has been treated with silanising agents to improve the adhesion of the inorganic fillers with the polymer thereby obtaining a certain agglomeration of the powder particles, these fillers, however, have merely a rather poor hardness, since these agglomerates are not hard and resistant because the cohesion by the silanising agents is not stable. Upon incorporation of these agglomerates into the monomer preparation, a renewed division occurs, and again only salve-like or powdery products are obtained.

From the DE-OS No. 14 67 437, relatively stable agglomerated silicic acids are known; their advantageous utilisation for the special requirements of dental materials is, however, in no way disclosed since only the application as delustrant for lacquer is described.

Therefore, it is the object of the invention to find a new reinforcing filler for dental materials essentially consisting of inorganic material which filler is practically colourless and can be blended in considerable quantity into the polymerizable monomer materials. In this connection, pastes shall be obtained which are plastically deformable in an easy way which pastes yield to well polishable shaped bodies of low thermal expansion coefficient and high abrasion resistance after the curing practically without shrinking.

According to the invention, this is achieved by using an inorganic filler in form of agglomerate of silicic acid having an average particle size of 0.5–50 $\mu$m, preferable 1–10 $\mu$m, which filler consists of primary particles of silicic acid having an average particle size of 1–100 nm. If necessary, the granular material can contain additional inorganic, oxidic constituents as e.g. aluminium oxide or boron oxide.

On the one hand the agglomerate material must be so stable that a redivision does not occur during the processing with the monomers and on the other hand should be hard to such a degree only that the shaped bodies are still polishable after polymerizing. The hardness of the filler can be adjusted in the course of the subsequently described method of production by the duration and especially by the temperature of the final annealing; therewith the suitable range of temperature amounts from approximately 600° C. up to more than 1200° C. Naturally, the temperature and annealing period must be adjusted to the respective combination silica gel/oxidic binding agent in order to achieve the desired values of hardness. This can be determined by the expert through simple tests.

The agglomerates of silicic acid can be produced with or without binding agent in different ways. For a cohesion of the primary particles with silicon dioxide, a method is suitable in which the micro-fine silicic acid which is obtained through precipitation or preferably through pyrogenic steps and whose particle size can amount between 1 to 100 nm, preferably between 5 to 50 nm, is premixed with a water glass solution, the mixture being then acidified, the mass being dried and slowly heated up to more than 600° C. Afterwards, it is washed with water thereby removing soluble fractions. After drying, the agglomerated material so obtained is adjusted to the requested granular size by milling and screening, if necessary.

In similar manner, a cohesion and stable agglomerating to an inorganic agglomerated material of silicic acid can be achieved which is suitable as filler by using a boric acid solution or alcoholic aluminium alcoholate solution. While the aluminium compounds cause the agglomeration probably through the formation of the binding agent aluminium oxide, the boron compounds obviously have primarily a catalytic effect for the cohesion of the primary particles within the agglomerated material, wherein the major part of the formed boron oxide is volatilized during the step of annealing without influencing the stability of the agglomerate. Although it was known from the DE-OS No. 27 16 225, to impregnate precipitated silicic acid with boric acid; the silicic acid serving as catalyst support for the boron oxide and as filler for organopolysiloxanes which are used as so-called bouncing putties.

This state of art, however, could thus not give any suggestion for the advantageous use for the special requirements of dental materials of this agglomerated material of silicic acid bound by boric acid.

According to another suitable method of production, the raw material is premixed with silicon tetrachloride and then is hydrolysed in moist atmosphere or by addition of water. The mixture obtained is slowly heated up to more than 600° C. wherein the hydrochloric acid formed evaporates. Afterwards, residual HCl is washed out and the requested agglomerate size is adjusted through milling and screening.

This method can be combined in such a manner that silicon tetrachloride is added to the mixture of the primery silicic acid and water glass. The further processing is then performed as described by drying and heating and subsequent washing out of soluble constituents as e.g. alkalichloride.

According to a further advantageous manner of production, the micro-fine silicic acid is premixed with organo-silicon compounds which preferably contain a plymerizable residue. If necessary, a polymerization catalyst in conventional concentration is added and the mixture is polymerized e.g. under action of heat. Afterwards, the mixture is slowly heated on air until the organic constituents are burned, and finally brought up to more than 600° C. After cooling down, the requested agglomerate size can be obtained through milling and screening.

Suitable organosilicon compounds are e.g.: vinyl trichlorosilane, vinyl trimethoxysilane, allyldimethylchlorosilane, $\gamma$-methacryloxypropyltrimethoxysilane, $\beta$-(3,4-epoxycyclohexyl)-ethyl-trimethoxysilane and $\gamma$-glycideoxypropyltrimethoxysilane. Even longer annealing of the micro-fine silicic acids above 800° C. leads to useful agglomerated materials without any binding additives.

The agglomerated material of silicic acid according to the invention can be easily mixed with the liquid polymerizable monomers. In this connection, the monofunctional, di-functional or polyfunctional derivates of the acrylic acid of methacrylic acid have proven useful as monomers, especially the esters. In advantageous manner, the filler according to the invention is used together with a fraction of non-agglomerated, microfine silicic acid of a particle size of 1-100 nm, preferably of 5-50 nm for adjustment of the consistency and for prevention of separation. Relative to the total material, the fraction of the material of the non-agglomerated silicic acid can be between 0.5 and 40%, preferably between 2-30% by weight.

The inorganic fraction of filler in the dental materials according to the invention shall amount as usually between 10 and 80%, preferably between 30 and 80% and especially preferably between 50 and 70% relative to the total material.

Prior to its application the agglomerated material of silica gel can be silanized to improve the cohesion with the polymer e.g. by treatment with trimethoxy-(3-methacryloxypropyl)-silane. For dental use, known organic or inorganic pigments and/or opacifiers are usually added to the material for matching to the natural teeth. As hardening catalysts i.a. organic peroxides like dibenzoyl peroxide, or azo-compounds like azo-bis-iso-butyronitrile can be used in these preparations. The redox systems, as e.g. dibenzoyl peroxide/N,N-bis-2-hydroxyethylxylidine or dibenzoyl-peroxide/barbituric acid derivates which redox systems are suitable for the cold hardening of vinyl-unsaturated monomers, are also appropriate.

As hardening catalysts, also substances can be employed, which initiate the polymerization after irradiation with UV-light or visible light as e.g. benzoinalkylethers, benzilmonoketales or aliphatic and aromatic 1,2-diketone compounds wherein the photopolymerization can be accelerated in a manner known per se through addition of activators like amines or organic phosphites.

After curing the polymerizable materials with the fillers according to the invention, the compressive strength of the shaped bodies is up to more than 20% higher than upon usage of fillers according to the state of art. The compressive strength amounts in the photopolymerisates up to more than 450 MPa instead of approximately 350 MPa. Moreover, the positive properties of the quartz filled shaped bodies, namely low thermal expansion, high colour stability, low water absorption are combined with the positive properties of the pre-known shaped bodies produced with micro-fine silicic acid, with regard to the polishing ability, in one material without obtaining any disadvantages. It could not be expected that through the usage of mechanically relatively stable agglomerates from the micro-fine silica gels and possibly purely inorganic binding agent as filler, in combination with polymerizable monomers, paste-like dental materials are obtained which have good consistency despite a high fraction of filler and are finishable to high luster after curing.

The agglomerated filler according to the invention is generally suitable for tooth restoration compositions, and thus not only for tooth filling preparations but also for such purposes for which such materials are usually used advantageously, e.g. for production of crowns, bridges, veneers and alike prosthetic dental appliances and also for the production of artificial teeth.

EXAMPLE 1

Agglomeration with water glass

The quantity of silica gel as mentioned below is kneaded into 100 g filtered soda water glass (approximately 39° Baume) and the mixture is adjusted to pH 5-6 with concentrated hydrochloric acid. Through addition of methanol, a kneadable consistency is obtained. After kneading for two hours, the methanol is removed at 60° C. and 200 torr and dried through heating at 120° C. Then, it is brought slowly to 800° C., the cooled product is ground and freed from soluble content of alkali by washing with water. Through repeated drying at 120° C., a pulverant filler is obtained (average agglomerate size approximately 5 μm).

| Number of product | primary silica gel | | | |
|---|---|---|---|---|
| | mode of production | specific surface ($m^2/g$) | average particle diameter (nm) | quantity (g) |
| 1 | pyrogenic | 50 | 40 | 60 |
| 2 | pyrogenic | 380 | 7 | 25 |
| 3 | precipitated | 110 | 28 | 60 |

EXAMPLE 2

Agglomeration with boric acid

A saturated, aqueous solution of boric acid is produced by decanting from the bottom sediments at approximately 78° C. In 468 g of this solution, 1400 g pyrogenic silicic acid (specific surface 50 m$^2$/g, average particle diameter 40 nm) are introduced under stirring at a temperature of above 80° C. during approximately 2 hours. Subsequently, it is stirred for 30 minutes and then the water is removed in the vacuum. The solid substance is dried at 120° C. and slowly heated up to 800° C. After milling in a ball mill, the obtained powder is extracted with water until the wash water is free of boron. Subsequently the filler is dried at 120° C. in the vacuum.

The average agglomerate size of the filler is approximately 4 μm.

EXAMPLE 3

Paste/Paste-preparation for production of tooth fillings

For production of the pastes, there are kneaded:
(A) 249.0 g of agglomerated silicic acid coloured tooth-like (average particle size 5 μm, average primary particle size 40 nm, binding agent SiO$_2$, <63 μm, silanized) and
33.0 g pyrogenic, non-agglomerated, silanized silica gel with a solution of
1.5 g N,N-bis-hydroxy-ethyl-3,5-di-t-butyl-aniline in 122.5 g 2,2-bis[p-(γ-hydroxy-propoxy-)phenyl]-propane dimethacrylate and
31.0 g bis-GMA
(B) 287.0 g of the silanized agglomerated silicic acid used in paste A) and
42.0 g pyrogenic, non-agglomerated, silanised silica gel with a solution of
4.0 g p-chlorobenzoylperoxide in 200.0 g 2,2-bis[p-(γ-hydroxy-propoxy-)phenyl]-propane dimethacrylate and
40.0 g bis-GMA By mixing equal parts of both pastes, a plastic mass is obtained which can be introduced and shaped easily in conventionally prepared tooth cavities. Approximately 2 minutes after mixing, the hardening starts which ends after approximately 3.5 minutes. The abrasion resistant filling can be finished to high luster by conventional dental procedures. The linear thermal expansion coefficient of the cured material is $45 \times 10^{-6} K^{-1}$.

EXAMPLE 4

Tooth filling material polymerizable by UV-light

A solution is prepared of:
20.0 g bis-hydroxymethyl-tricyclo[5.2.1.0.$^{2,6}$]-decane-di-methacrylate (stabilised with 200 ppm p-methoxyphenol and 200 ppm jonol)
120.0 mg benzildimethylketale and
100.0 mg didecyl-phenyl-phosphite Furthermore, a powder mixture is prepared of
14.0 g silanized agglomerated silicic acid according to the invention (average particle size 6 μm, average primary particle size 40 nm, binding agent B$_2$O$_3$, <63 μm) coloured tooth-like
10.0 g silanized, non-agglomerated, pyrogenic silica gel and
2.0 g finely pulverized calciumfluoride.

10.5 g of the solution and 18 g of the powder mixture are kneaded to a homogenous tooth filling material. After an exposure time of 20 sec. with a conventional UV-irradiation equipment (UVIOLITE, Firma ESPE) with an output of 70 mW the material is cured in a layer thickness of approximately 3 mm. The abrasion-resistant material is finishable to high luster and has a linear thermal expansion coefficient of $45 \times 10^{-6} K^{-1}$.

The compressive strength is 400 MPa measured at exposed test samples of 2×2×4 mm after storage under water at 36° C. for 24 hours.

COMPARATIVE EXPERIMENT 1

In a mixture of
14.0 g bis-hydroxymethyl-tricyclo[5.2.1.0.$^{2,6}$]-decane-diacrylate (stabilised with 200 ppm-p-methoxyphenol and 200 ppm jonol)
6.0 g bis-GMA
9.0 g silanized, pyrogenic silicic acid (specific surface 50 m$^2$/g)
0.3 g methyl-diethanolamine-dimethacrylate and
0.03 g camphor quinone a quantity of commercial silicic acids on the one hand and of agglomerated material according to the invention on the basis of these silicic acids on the other hand is introduced which quantity is determined by preliminary tests to result in a paste like material. The test samples obtained after exposure with a commercial dental irradiation equipment emitting visible light (ELIPAR-equipment, Firma ESPE) show the physical properties listed in the following table.

| SILICIC ACID | | | | | | Inorganic | |
|---|---|---|---|---|---|---|---|
| type | average particle size [nm] | agglomerated | Workable as tooth filling | Surface hardness [MPa] | Thermal expansion [K$^{-1}$] | Flexural strength [MPa] | fraction [% of total material] | REMARKS |
| pyrogenic | 40 | no | no (stringy) | 128 | 62 × 10$^{-6}$ | 65 | 58 | Commercial product "AEROSIL OX50" Firma DEGUSSA |
| pyrogenic | 40 | yes | good | 202 | 52 × 10$^{-6}$ | 85 | 60 | |
| pyrogenic | 7 | no | no (stringy) | 160 | 78 × 10$^{-6}$ | 72 | 32 | Commercial product "AEROSIL 380" Firma DEGUSSA |
| pyrogenic | 7 | yes | good | 255 | 46 × 10$^{-6}$ | 93 | 68 | |
| precipitated | 8 | no | no (stringy) | 132 | 102 × 10$^{-6}$ | 81 | 22 | Commerical product "FK310" Firma DEGUSSA |
| precipitated | 8 | yes | good | 191 | 48 × 10$^{-6}$ | 114 | 70 | |

Only the use of the agglomerated silicic acids according to the invention yields pastes which can be processed as tooth fillings. The surface hardness of the polymerisates is increased to more than 50%, the thermal expansion is decreased about 15-50%, the flexural strength is increased to more than 30%.

COMPARATIVE EXPERIMENT 2

The physical data of filling A (according to the invention, example 3) are compared with the commercial preparations B, C and D, whose basis are the following fillers:

B—glass powder, average particle size approximately 10 μm (Adaptic Radiopaque, Johnson & Johnson)

C—glass powder, average particle size approximately 10 μm mixed with micro-fine silicic acid (Miradapt, Johnson & Johnson)

D—polymer covered micro-fine silicic acid, average particle size approximately 40 nm (Silar, 3M Co.)

| | Preparation | | | |
|---|---|---|---|---|
| | A | B | C | D |
| Compressive strength [MPa] | 370 | 240 | 320 | 290 |
| Flexural strength [MPa] | 80 | 65 | 85 | 50 |
| Stability of colour | superior | good | good | poor |
| Polishability | superior | bad | poor⊕ | superior |

⊕ = only with special grinding instruments

The tooth filling A according to the invention combines the advantageous properties of conventional materials with the glass fillers (preparation B) as well as with the polymer covered micro-fine silicic acids (preparation D); this result is not achieved by the mere mixture of both filler types (preparation C).

Only the material according to the invention is polishable together with high compressive strength and flexural strength and has superior colour stability.

We claim:

1. A dental material comprising a polymerizable monomer and an inorganic filler, said filler comprising agglomerates of silicic acid having an average agglomerate size of 0.5 to 50 μm, said agglomerates comprising primary particles of silicic acid having an average particle size of 1 to 100 nm.

2. A dental material according to claim 1, wherein the average agglomerate size of said agglomerates is 1 to 10 μm.

3. A dental material according to claim 1, further comprising non-agglomerated, micro-fine silicic acid having an average particle size of 1 to 100 nm.

4. A dental material according to claim 3, wherein said non-agglomerated silicic acid has an average particle size of 5 to 50 nm.

5. A dental material according to claim 3, wherein said non-agglomerated silicic acid comprises 0.5 to 40% by weight of the total material.

6. A dental material according to claim 5, wherein said non-agglomerated silicic acid comprises 2 to 30% by weight of the total material.

7. A dental material according to claim 1, wherein said inorganic filler comprises 10 to 80% by weight of the total material.

8. A dental material according to claim 7, wherein said inorganic filler comprises 30 to 80% by weight of the total material.

9. A dental material according to claim 8, wherein said inorganic filler comprises 50 to 70% by weight of the total material.

10. A dental material according to claim 1, wherein said polymerizable monomer comprises a mono-functional, di-functional or poly-functional derivative of acrylic or methacrylic acid.

11. A dental material according to claim 10, wherein said derivative is an ester.

12. A dental material according to claim 1, wherein the average agglomerate size of said agglomerates is about 5 μm and the average particle size of said primary particles is about 40 nm.

13. A dental material according to claim 1, wherein the average agglomerate size of said agglomerates is about 6 μm and the average particle size of said primary particles is about 40 nm.

14. A cured, shaped body prepared from a dental material as claimed in claim 1.

15. A dental filling material according to claim 1, wherein said agglomerates of silicic acid are silanized.

16. A dental filling material according to claim 3, wherein said non-agglomerated, micro-fine silicic acid is silanized.

* * * * *